(12) United States Patent
Zhong et al.

(10) Patent No.: US 9,861,671 B2
(45) Date of Patent: Jan. 9, 2018

(54) COMPOSITION FOR PREVENTING AND TREATING AIDS AND PREPARATION METHOD THEREOF

(71) Applicant: JIANGZHONG PHARMACEUTICAL CO., LTD., Nanchang, Jiangxi (CN)

(72) Inventors: Hongguang Zhong, Nanchang (CN); Minzhi Yi, Nanchang (CN); Jianzhong Lu, Nanchang (CN)

(73) Assignee: Jiangzhou Pharmaceuticals Co., Ltd., Nanchang (CN)

( * ) Notice: Subject to any disclaimer, the term of this patent is extended or adjusted under 35 U.S.C. 154(b) by 48 days.

(21) Appl. No.: 14/403,990

(22) PCT Filed: May 27, 2013

(86) PCT No.: PCT/CN2013/000620
§ 371 (c)(1),
(2) Date: Nov. 25, 2014

(87) PCT Pub. No.: WO2013/177945
PCT Pub. Date: Dec. 5, 2013

(65) Prior Publication Data
US 2015/0150928 A1 Jun. 4, 2015

(30) Foreign Application Priority Data

May 29, 2012 (CN) .......................... 2012 1 0169737

(51) Int. Cl.
```
A61K 36/00      (2006.01)
A61K 36/481     (2006.01)
A61K 36/068     (2006.01)
A61K 36/074     (2006.01)
A61K 36/258     (2006.01)
A61K 36/344     (2006.01)
A61K 36/36      (2006.01)
A61K 36/73      (2006.01)
A61K 9/08       (2006.01)
A61K 9/00       (2006.01)
A61K 9/14       (2006.01)
A61K 9/16       (2006.01)
A61K 9/20       (2006.01)
A61K 9/48       (2006.01)
```
(52) U.S. Cl.
CPC .......... *A61K 36/481* (2013.01); *A61K 36/068* (2013.01); *A61K 36/074* (2013.01); *A61K 36/258* (2013.01); *A61K 36/344* (2013.01); *A61K 36/36* (2013.01); *A61K 36/73* (2013.01); *A61K 9/0056* (2013.01); *A61K 9/0095* (2013.01); *A61K 9/08* (2013.01); *A61K 9/141* (2013.01); *A61K 9/1605* (2013.01); *A61K 9/2004* (2013.01); *A61K 9/4841* (2013.01)

(58) Field of Classification Search
CPC ...................................................... A61K 36/00
USPC ........................................................ 424/725
See application file for complete search history.

(56) References Cited

U.S. PATENT DOCUMENTS

2005/0129780 A1   6/2005   Holcomb-Halstead et al.

FOREIGN PATENT DOCUMENTS

| CN | 1055486 A   | 10/1991 |
|----|-------------|---------|
| CN | 1413727 A   | 4/2003  |
| CN | 1428166 A   | 7/2003  |
| CN | 101292742 A | 10/2008 |
| CN | 101292742 A | 10/2008 |
| CN | 101590177 A | 12/2009 |
| CN | 101590177 A | 12/2009 |
| CN | 102125649 A | 7/2011  |
| CN | 102274258 A | 12/2011 |
| CN | 102274258 A | 12/2011 |
| CN | 102274259 A | 12/2011 |
| CN | 102274259 A | 12/2011 |
| CN | 102406163   | 4/2012  |
| CN | 102406163 A | 4/2012  |

OTHER PUBLICATIONS

Second Office Action dated Jun. 30,2016 for counterpart Chinese patent application No. 201210169737.7.
International Written Opinion with English translation for International Patent Application No. PCT/CN13/00620, dated Aug. 29, 2013; 18 pages.
Database WPI Week 200363 Thomson Scientific,London,GB;AN 2003-664281; XP002744929; 1 page.

(Continued)

*Primary Examiner* — Michael V Meller
(74) *Attorney, Agent, or Firm* — Loza & Loza, LLP; Michael F. Fedrick

(57) ABSTRACT

The present invention relates to a pharmaceutical composition made from the following raw materials or from water and/or alcohol extracts of the following raw materials in parts by weight: 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of *Cordyceps*, and optionally one or more of 5 to 90 parts of Flos Rosae Rugosae, 5 to 150 parts of *Ganoderma* spore powder, 10 to 400 parts of Radix Pseudostellariae, 3 to 400 parts of Radix *Codonopsis* and 3 to 400 parts of Radix Astragali. Clinical trials demonstrate that the composition can significantly reduce HIV virus load in patients, increase the number of CD4+ cells, enhance the immunity of patients, has no considerable toxic and side effects, and is suitable for long-term use.

24 Claims, No Drawings

(56) References Cited

OTHER PUBLICATIONS

Database WPI Week 201167 Thomson Scientific,London,GB;AN 2011-K35736; XP002744935; 3 pages.
Database WPI Week 200355 Thomson Scientific,London,GB;AN 2003-578173; XP002744936; 1 page.
Extended European Search Report for 13796943.2 dated Oct. 28, 2015; 7 pages.
Ponomariov, V.D. Ekstragirovanie lekarstvennogo syrya [Extraction of drug raw materials], Moscow, Medicina, pp. 115-120 (1976).
Russian Patent Application No. 2014151159, Office Action (dated Oct. 18, 2016).
Office action dated Nov. 4, 2015 for counterpart Chinese patent application No. 201210169737.7.
Search report dated Nov. 4, 2015 for counterpart Chinese patent application No. 201210169737.7.
Li Yun et al., "Status and Prospect of Traditional Chinese Medicine in the Prevention and Treatment for Aids," Natural Product Research and Development, vol. 15, No. 3, pp. 273-276 (2003).
Russian Patent Appln. No. 2014151159, Office Action dated Jun. 9, 2017.
Jiang et al., "Isolation of adenosine, iso-sinensetin and dimethylguanosine with antioxidant and HIV-1 protease inhibiting activities from fruiting bodies of Cordyceps militaris." Phytomedicine 18(2-3):189-93 (Jan. 15, 2011).
Huie et al., "Chromatographic and electrophoretic methods for Lingzhi pharmacologically active components." J. of Chromatography B. vol. 812, Issues 1-2, pp. 241-257 (Dec. 5, 2004).
Kim et al., "Panax ginseng as a potential immunomodulator: studies in mice." Immunopharmacology & Immunotoxicology 12(2), 257-276 (1990).

COMPOSITION FOR PREVENTING AND TREATING AIDS AND PREPARATION METHOD THEREOF

CROSS-REFERENCE TO RELATED APPLICATIONS

This application is the U.S. national stage of International Patent Application No. PCT/CN2013/000620, filed on May 27, 2013 and entitled COMPOSITION FOR PREVENTING AND TREATING AIDS AND PREPARATION METHOD THEREOF, which claims the benefit of priority under 35 U.S.C. §119 from Chinese Patent Application No. 201210169737.7, filed May 29, 2012. The disclosures of the foregoing applications are incorporated herein by reference in their entirety.

TECHNICAL FIELD

The present invention relates to a composition for prevention and treatment of AIDS and method for preparing the composition.

BACKGROUND ART

Acquired Immune Deficiency Syndrome (AIDS) is a syndrome in a human where immunodeficiency is caused by infection with Human Immunodeficiency Virus (HIV), which is accompanied by a series of opportunistic infections and tumors and may even lead to death in severe cases. AIDS is a serious threat to the lives of human beings; and over 70 million people in total have been affected with HIV over the last 30 years since AIDS was first confirmed by the Centers for Disease Control and Prevention of US in 1991, among which over 2.8 million were dead. Researchers all over the world have been arduously seeking medicaments for treating AIDS, but so far there has been neither a specific drug developed to cure AIDS nor an effective vaccine useful for preventing AIDS. A therapy with confirmed positive efficacy in western medicine is the Highly Active Antiretroviral Therapy (HAART, the cocktail therapy). Although this therapy significantly decreases the morbidity and mortality rate of AIDS, the development of combinational use of drugs is greatly limited, and the antiviral therapy is not successful in as many as 60% patients because of compliance, toxicity, drug resistance issues and the like. In addition, the cocktail therapy involves expensive drugs that are far beyond what an ordinary patient can afford. Chinese medicine, the traditional medicine in China, has played an essential role in prophylactic and therapeutic treatment of diseases for thousands of years. Recently, with sustained efforts of practicers in traditional Chinese medicine, promising progress has been made in prevention and treatment of AIDS with Chinese medicine. Therefore, to keep exploring the precious treasury of traditional Chinese medicine and seeking effective methods and medicaments for preventing and treating AIDS remains a primary goal of researchers in traditional Chinese medicine.

SUMMARY OF THE INVENTION

The objective of the present invention is to provide a composition for preventing and treating AIDS and the preparation method thereof.

In accordance with the present invention, we select and combine raw materials *Ganoderma*, Radix Panacis Quinquefolii or Radix Et Rhizoma Ginseng, fermented *Cordyceps sinensis* powder and/or *Cordyceps*, and we surprisingly found that such a composition were capable of preventing and treating AIDS.

The present invention relates to a composition for preventing and treating AIDS, characterized in that the composition is substantially made from the following raw materials or from water and/or alcohol extracts of these raw materials as active components in parts by weight: 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of *Cordyceps*.

In accordance with the present invention, preferred are 20 to 120 parts of *Ganoderma*, 10 to 90 parts of Radix Panacis Quinquefolii or Radix Et Rhizoma Ginseng, 3 to 60 parts of fermented *Cordyceps sinensis* powder and/or 3 to 90 parts of *Cordyceps*.

More preferred are 40 parts of *Ganoderma*, 30 parts of Radix Panacis Quinquefolii or Radix Et Rhizoma Ginseng, 20 parts of fermented *Cordyceps sinensis* powder and/or 6.7 parts of *Cordyceps*.

The composition of the present invention may further comprise additional materials that do not compromise the efficacy of the present invention or water and/or alcohol extracts of these additional materials, as follows in parts by weight: one of 5 to 90 parts of Flos Rosae Rugosae, 5 to 150 parts of *Ganoderma* spore powder, 10 to 400 parts of Radix Pseudostellariae, 3 to 400 parts of Radix *Codonopsis* and 3 to 400 parts of Radix Astragali, or any combination thereof.

Preferred is one of 10 to 60 parts of Flos Rosae Rugosae, 10 to 120 parts of *Ganoderma* spore powder, 20 to 200 parts of Radix Pseudostellariae, 20 to 200 parts of Radix *Codonopsis* and 20 to 200 parts of Radix Astragali, or any combination thereof.

More preferred is one of 30 parts of Flos Rosae Rugosae, 30 parts of *Ganoderma* spore powder, 40 parts of Radix Pseudostellariae, 40 parts of Radix *Codonopsis* and 40 parts of Radix Astragali, or any combination thereof.

Preferably, the composition of the present invention comprises 5 to 200 parts of *Ganoderma*, 5 to 150 parts of Radix Panacis Quinquefolii or Radix Et Rhizoma Ginseng, 1 to 90 parts of fermented *Cordyceps sinensis* powder and/or 1 to 120 parts of *Cordyceps*, and 5 to 90 parts of Flos Rosae Rugosae.

More preferred are 20 to 120 parts of *Ganoderma*, 10 to 90 parts of Radix Panacis Quinquefolii or Radix Et Rhizoma Ginseng, 3 to 60 parts of fermented *Cordyceps sinensis* powder and/or 3 to 90 parts of *Cordyceps*, and 10 to 60 parts of Flos Rosae Rugosae.

More preferred are 40 parts of *Ganoderma*, 30 parts of Radix Panacis Quinquefolii or Radix Et Rhizoma Ginseng, 20 parts of fermented *Cordyceps sinensis* powder and/or 6.7 parts of *Cordyceps*, and 30 parts of Flos Rosae Rugosae.

In accordance with the present invention, Radix Pseudostellariae, Radix *Codonopsis*, or Radix Astragali may be used instead of Radix Panacis Quinquefolii or Radix Et Rhizoma Ginseng.

The term "*Ganoderma*", as used herein, refers to the dry sporocarp of fungal species *Ganoderma lucidum* (Leyss. ex Fr.) Karst. or *Ganoderma sinense* Zhao, Xu et Zhang of the family Polyporaceae. It has a sweet taste and a plain nature, is involved in the heart, lung, liver and kidney channels, and has the effects of nourishing physical strength and calming and tranquillizing the mind. The term "Radix Et Rhizoma Ginseng", as used herein, refers to the dry root and rootstock of the plant species *Panax ginseng* C. A. Mey. of the family Araliaceae. It may be various types of ginseng, such as garden ginseng, wild ginseng, dried fresh ginseng, dried fresh wild ginseng, sugar-processed ginseng, and red ginseng. The term Folium Ginseng refers to the dry leaves of the plant species *Panax ginseng* C. A. Mey. of the family Araliaceae. The term "Radix Panacis Quinquefolii", as used herein, also known as American ginseng, *huaqishen*, *yangshen*, or *guangdongshen*, refers to the dry root of the plant species *Panax quinquefolium* L. of the family Araliaceae. It has a sweet and slightly bitter taste and a cool nature, is involved in the heart, lung and kidney channels, and has the effects of invigorating Qi, nourishing Yin, clearing heat, and promoting fluid production. The term "*Cordyceps*", as used herein, refers to a dry complex from a dead body of an insect larva of the family Hepialidae and a stroma of the fungal species *Cordyceps sinensis* (Berk.) sace. of the family Clavicipitaceae parasitizing on the larva.

The term "fermented *Cordyceps sinensis* powder", as used herein, refers to a product of strains that were originally isolated from the natural *Cordyceps* of *Cordyceps sinensis* (Berk.) sace. and have been cultured under fermentation conditions, wherein the strains may be one of *Paecilomyces hepialli* Chen et Dai, sp.nov, *Hirsutella sinensis* Liu, Guo, Yu-et Zeng, sp.nov, *Cephalosporium sinensis* Chen sp.nov, *Mortiscrslla hepialid* C. T. & B. liu, *Paecilomyces sinensis* Chen, Xiao et Shi, sp.nov, *Tolypocladium sinensis* C. lan Li, *Cephalosporium sinens* Chen sp.nov, *Scytalidium hepialii* C. L. Li, *Chrysosporium sinens* Z. Q. liang, *Verticillium sinens* Wamg sp.nov, *Cephalosporium acremonium* Corda, Icones Fungorum, *Synnematium sinensis* Yin & Shen, *Isaria farinose* (Holmsk.) Fr. Systema Mycologicum, *Metarhizium anisopliae* (Metsch) Sorokin, *Hirsutella hepialid* Chen et Shen, *Sporothrix insectorum* de Hong & H. C. Evans, *Gliocladium roseum* (link) Thom and *Mortierella* sp., or any combination thereof.

The strain from which the fermented *Cordyceps sinensis* powder of the present invention is derived is preferably one of *Paecilomyces hepialli* Chen et Dai, sp.nov, *Mortiscrslla hepialid* C. T. & B. liu, *Synnematium sinensis* Yin & Shen, *Gliocladium roseum* (link) Thom, *Mortierella* sp., *Cephalosporium sinensis* Chen sp.nov or *Hirsutella sinensis* Liu, Guo, Yu-et Zeng, sp.nov, or any combination thereof.

The term "Flos Rosae Rugosae", as used herein, refers to the dry flower bud of the plant species *Rosa rugosa* Thumb or *Rose rugosacv* Plena of the family Rosaceae. It has a pungent, sweet and slightly bitter taste and a warm nature, and represents a warm-natured drug. Its most significant effects are to activate Qi flowing, resolve stagnation, harmonize the blood, and relieve pain.

The term "Radix *Codonopsis*" refers to the dry root of the plant species *Codonopsis pilosula* (Franch.) Nannf., *Codonopsis pilosula* Nannf.var.modesta (Nannf.) L. T. Shen, or *Codonopsis tangshen* Oliv. of the family Campanulaceae.

The term "Radix Pseudostellariae" used here in refers to the dry tuberous root of the plant species *Pseudostellaria heterophylla* (Miq.) Pax ex Pax et Hoffm. of the family Cargophyllaceae.

The term "Radix Astragali" refers to the dry root of the plant species *Astragalus membranaceus* (Fisch) Bge.var. mongholicus (Bge) Hsiao or *Astragalus membranaceus* (Fisch) Bge. of the family Fabaceae.

The *Ganoderma* spore powder according to the present invention is preferably sporoderm-broken *Ganoderma* spore powder.

The *Ganoderma* spore powder according to the present invention is sexual reproductive cells of *Ganoderma*, i.e., basidiospore powder.

The alcohol according to the present invention may be ethanol at a concentration of 5% to 95%.

The composition according to the present invention can be prepared into a dosage form by adding excipients acceptable in health care products, medicaments or products.

The dosage form may be any one of a tablet, an oral liquid, a granule, a capsule, an electuary, a dripping pill, a pill, a powder, a lozenge, a fluid extract, an extract, an injection, and a syrup.

The present invention provides use of a composition comprising *Ganoderma*, Radix Panacis Quinquefolii or Radix Et Rhizoma Ginseng, fermented *Cordyceps sinensis* powder and/or *Cordyceps*, a composition made from raw materials comprising *Ganoderma*, Radix Panacis Quinquefolii or Radix Et Rhizoma Ginseng, fermented *Cordyceps sinensis* powder and/or *Cordyceps*, or a composition made from *Ganoderma*, Radix Panacis Quinquefolii or Radix Et Rhizoma Ginseng, fermented *Cordyceps sinensis* powder and/or *Cordyceps*, in the manufacture of a health care product, a medicament or a product for preventing and treating AIDS.

Also provided is use of a composition prepared by adding any one or more components of Flos Rosae Rugosae, *Ganoderma* spore powder, *Ganoderma* spore oil, Radix Pseudostellariae, Folium Ginseng, Radix *Codonopsis*, and Radix Astragali to a composition comprising *Ganoderma*, Radix Panacis Quinquefolii or Radix Et Rhizoma Ginseng, fermented *Cordyceps sinensis* powder and/or *Cordyceps*, or to a composition made from raw materials comprising *Ganoderma*, Radix Panacis Quinquefolii or Radix Et Rhizoma Ginseng, fermented *Cordyceps sinensis* powder and/or *Cordyceps*, or to a composition made from *Ganoderma*, Radix Panacis Quinquefolii or Radix Et Rhizoma Ginseng, fermented *Cordyceps sinensis* powder and/or *Cordyceps*, in the manufacture of a health food product, a medicament or a product for preventing and treating AIDS.

Also provided is use of a composition comprising *Ganoderma*, Radix Panacis Quinquefolii or Radix Et Rhizoma Ginseng, fermented *Cordyceps sinensis* powder and/or *Cordyceps*, and Flos Rosae Rugosae, a composition made from raw materials comprising *Ganoderma*, Radix Panacis Quinquefolii or Radix Et Rhizoma Ginseng, fermented *Cordyceps sinensis* powder and/or *Cordyceps*, and Flos Rosae Rugosae, or a composition made from *Ganoderma*, Radix Panacis Quinquefolii or Radix Et Rhizoma Ginseng, fermented *Cordyceps sinensis* powder and/or *Cordyceps*, and Flos Rosae Rugosae, in the manufacture of a health care product, a medicament or a product for preventing and treating AIDS.

Also provided is use of a composition prepared by adding any one or more components of *Ganoderma* spore powder, *Ganoderma* spore oil, Radix Pseudostellariae, Folium Ginseng, Radix *Codonopsis*, and Radix Astragali to a composition comprising *Ganoderma*, Radix Panacis Quinquefolii or Radix Et Rhizoma Ginseng, fermented *Cordyceps sinensis* powder and/or *Cordyceps*, and Flos Rosae Rugosae, or to a composition made from raw materials comprising *Ganoderma*, Radix Panacis Quinquefolii or Radix Et Rhizoma Ginseng, fermented *Cordyceps sinensis* powder and/or *Cordyceps*, and Flos Rosae Rugosae, or to a composition made from *Ganoderma*, Radix Panacis Quinquefolii or Radix Et Rhizoma Ginseng, fermented *Cordyceps sinensis* powder and/or *Cordyceps*, and Flos Rosae Rugosae, in the manufacture of a health care product, a medicament or a product for preventing and treating AIDS.

The term "a product" in "a health care product, a medicament or a product" as mentioned above includes other products not encompassed in health care products or medicaments, including any article using the composition according to the present invention, for example, essential oils, incense products, and pillows.

A process for preparing the water and/or alcohol extracts of the raw materials for the composition according to the present invention comprises the steps of
1) weighing out prescribed amounts of traditional Chinese drugs as the raw materials; and
2) extracting the raw materials under reflux with ethanol at a concentration of 5 to 95% or water in an amount of 6 to 13 folds to obtain a liquid extract as the active ingredient, and adding excipient(s) to prepare various dosage forms.

The process for preparing the water and/or alcohol extracts of the raw materials for the composition according to the present invention may comprise the steps of
1) weighing out prescribed amounts of traditional Chinese drugs as the raw materials, adding 5% to 95% ethanol thereto to carry out extraction, recovering ethanol from the extraction liquid, to afford Extract I;
2) evaporating ethanol from the residual drugs, adding water in an amount of 6 to 13 folds to carry out extraction, to afford Extract II; and
3) combining Extract I and Extract II, carrying out filtration, concentrating the filtrate to an appropriate amount, adding pharmaceutically conventional auxiliary agent(s) to prepare a desired formulation by a pharmaceutically conventional process.

The process for preparing the water and/or alcohol extracts of the raw materials for the composition according to the present invention may also comprise the steps of
1) raw material preparation: weighing out prescribed amounts of traditional Chinese drugs as the raw materials;
2) extraction and concentration: soaking the weighed Chinese drug raw materials in 6 to 13-fold water for 20 to 60 minutes, then decocting the mixture 3 times by heating with each decoction lasting for 0.5 to 2 hours, carrying out filtration, combining the filtrates and concentrating it to an appropriate amount, cooling the concentrate and subjecting it to high-speed centrifugation to remove impurities, and reserving the product until use;
3) formulation preparation: preparing the concentrate from which impurities have been removed, alone or together with medicinally acceptable auxiliary agent(s), into a desired formulation by a pharmaceutically conventional process.

In order to provide a better understanding of the spirit of the present invention, clinical trials using the composition consisting of Ganoderma, Radix Panacis Quinquefolii or Radix Et Rhizoma Ginseng, fermented Cordyceps sinensis powder and/or Cordyceps, as well as the results thereof, are described hereinafter to demonstrate the effectiveness of the composition in prevention and treatment of AIDS.

Similarly, addition of any one of Flos Rosae Rugosae, Ganoderma spore powder, Radix Pseudostellariae, Radix Codonopsis, and Radix Astragali, or any combination thereof, can also lead to the same pharmacologic actions, with different amounts in use.

Clinical efficacy proves that the composition of the present invention can significantly reduce the virus load of HIV in a patient, increase the number of CD4+ cells, enhance the immunity of the patient, has no toxic and side effect, and is suitable for long-term use by AIDS patients. Details of the clinical trials are as follows:

I. Case Selection
1. Enrollment Criteria
1) persons infected with HIV who show positive for HIV antibodies in laboratory examination;
2) at the age of 18 to 60;
3) having signed an informed consent, and volunteering to enter the clinical observation.

2. Exclusion Criteria
1) women in gestational period or breastfeeding period;
2) patients with primary diseases in vital organs;
3) persons who have participated in other clinical trials within a month;
4) persons who have been taking other medicaments currently known to have anti-HIV effects.

II. Treatment Regimen
1. Test samples: test samples were prepared according to the prescription and preparation method in Example 1, Example 2, Example 3, Example 4, Example 5 and Example 6 below.
2. Dosage plan: each test group was given a corresponding test sample, i.e., the group of Example 1 took 1 bottle (200 ml/bottle) of the sample prepared according to the prescription and preparation method in Example 1, once per day, and so do other groups.
3. Duration of the treatment: 2 months.
4. During the observation period, intake of other traditional Chinese medicine formulations or heath foods was not allowed.

III. Items of Observation
Copy number of HIV RNA (copies/ml); CD4+ lymphocyte count.

IV. Assessment of Efficacy
Standards for Assessment:
Effective: a gradual increase in CD4+, with an increase in CD4+>30% or 50 cells/mm$^3$, or a decrease in viral load >0.5 log/mL or to an undetectable level after treatment;
Stable: no change or a gradual increase in CD4+, with an increase or decrease in CD4+<30% or 50 cells/mm$^3$, or an increase or decrease in viral load <0.5 log/mL after treatment;
Ineffective: a decrease in CD4+>30% or 50 cells/mm$^3$ and a continuous increase in the level of viral load, with an increase in copy number >0.5 log/mL.

V. Clinical Results
Observations on the efficacy of the composition of the present invention in 149 cases of AIDS patients

| | | Results | | | |
|---|---|---|---|---|---|
| Group | Total Number of Cases | Number of Effective | Number of Stable | Number of Ineffective | Overall Effectiveness (%) |
| Example 1 group | 26 | 12 | 9 | 5 | 80.77 |
| Example 2 group | 25 | 11 | 12 | 2 | 92 |
| Example 3 group | 25 | 10 | 9 | 6 | 76 |
| Example 4 group | 22 | 8 | 10 | 4 | 81.82 |
| Example 5 group | 27 | 11 | 11 | 5 | 81.48 |
| Example 6 group | 24 | 10 | 10 | 4 | 83.33 |

Note:
Overall Effectiveness = (number of effective cases + number of stable cases)/Total Number of Cases As seen from the above results, the overall effectiveness of the compositions of the present invention is 80.77%, 92%, 76%, 81.82%, 81.48% and 83.33%, respectively, indicating a therapeutic effect of the composition of the present invention on AIDS.

DETAILED DESCRIPTION

Example 1

300 g Radix Panacis Quinquefolii, 400 g *Ganoderma*, 67 g *Cordyceps*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The *Cordyceps* was pulverized and then put in a cloth bag. The above five drugs were soaked in water for 1 h, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 2

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 20 min, and decocted 3 times by heating. Each decoction lasted for 1 h, with a 9-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 3

380 g *Ganoderma*, 320 g Radix Panacis Quinquefolii, and 210 g fermented *Cordyceps sinensis* powder were weighed out. The Radix Panacis Quinquefolii and *Ganoderma* were sliced and the fermented *Cordyceps sinensis* powder was put in a cloth bag. The above three drugs were soaked in water for 30 min, and decocted 3 times by heating. The first decoction lasted for 2 h with a 13-fold amount of water added, and the following decoctions each lasted for 1 h with a 10-fold amount of water added for each. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 4

350 g *Ganoderma*, 310 g Radix Panacis Quinquefolii, and 70 g *Cordyceps* were weighed out. The Radix Panacis Quinquefolii and *Ganoderma* were sliced, and the *Cordyceps* pulverized and then put in a cloth bag. The above three drugs were soaked in water for 30 min, and decocted 2 times by heating. The first decoction lasted for 2 h with a 12-fold amount of water added, and the second decoction lasted for 1.5 h with an 8-fold amount of water added. The two liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 5

400 g *Ganoderma*, 300 g Radix Panacis Quinquefolii, 67 g *Cordyceps*, and 200 g fermented *Cordyceps sinensis* powder were weighed out. The Radix Panacis Quinquefolii and *Ganoderma* were sliced and the fermented *Cordyceps sinensis* powder was put in a cloth bag. The *Cordyceps* was pulverized and then put in a cloth bag. The above four drugs were soaked in water for 40 min, and decocted 3 times by heating. The first decoction lasted for 2 h with a 14-fold amount of water added, and the following decoctions each lasted for 1 h with a 12-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 6

290 g Radix Panacis Quinquefolii, 370 g *Ganoderma*, 53 g *Cordyceps*, and 250 g Flos Rosae Rugosae were weighed out. The Radix Panacis Quinquefolii and *Ganoderma* were sliced, and the *Cordyceps* was pulverized and then put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 7

1.5 kg Radix Panacis Quinquefolii, 2.0 kg *Ganoderma*, 1.0 kg fermented *Cordyceps sinensis* powder (*Hirsutella sinensis* Liu, Guo, Yu-et Zeng, sp.nov), and 1.5 kg Flos Rosae Rugosae were weighed out. The Radix Panacis Quinquefolii and *Ganoderma* were sliced and the fermented *Cordyceps sinensis* powder was put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder.

Example 8

2.0 kg *Ganoderma*, 1.5 kg Radix Panacis Quinquefolii, 0.33 kg *Cordyceps*, 1.0 kg fermented *Cordyceps sinensis* powder (*Paecilomyces hepialli* Chen et Dai, sp.nov), and 1.5 kg Flos Rosae Rugosae were weighed out. The Radix Panacis Quinquefolii and *Ganoderma* were sliced, and the *Cordyceps* was pulverized and put in a cloth bag together with the fermented *Cordyceps sinensis* powder. The above drugs were soaked in water for 30 min, and decocted 3 times by heating. The first decoction lasted for 2 h with a 12-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder.

Example 9

150 g Radix Panacis Quinquefolii, 90 g fermented *Cordyceps sinensis* powder (*Hirsutella hepialid* Chen et Shen), 120 g *Cordyceps*, 200 g *Ganoderma*, and 90 g Flos Rosae Rugosae were weighed out. The Radix Panacis Quinquefolii and *Ganoderma* were sliced, and the *Cordyceps* was pulverized and put in a cloth bag together with the fermented *Cordyceps sinensis* powder. The above drugs were soaked in water for 1 h, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 10

500 g Radix Et Rhizoma Ginseng, 100 g fermented *Cordyceps sinensis* powder (*Synnematium sinensis* Yin & Shen), 500 g *Ganoderma*, and 500 g Flos Rosae Rugosae were weighed out. The Radix Et Rhizoma Ginseng and *Ganoderma* were sliced, and the fermented *Cordyceps sinensis* powder was put in a cloth bag. The above four drugs were soaked in water for 30 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 11

500 g Radix Panacis Quinquefolii, 100 g fermented *Cordyceps sinensis* powder (*Hirsutella sinensis* Liu, Guo, Yu-et Zeng, sp.nov), 500 g *Ganoderma*, and 500 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 12

150 g Radix Panacis Quinquefolii, 120 g *Cordyceps*, 200 g *Ganoderma*, and 90 g Flos Rosae Rugosae were weighed out. The Radix Panacis Quinquefolii and *Ganoderma* were sliced, and the *Cordyceps* was pulverized and then put in a cloth bag. The above four drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 13

150 g Radix Et Rhizoma Ginseng, 90 g fermented *Cordyceps sinensis* powder (*Gliocladium roseum* (link) Thom), 200 g *Ganoderma*, and 90 g Flos Rosae Rugosae were weighed out. The Radix Et Rhizoma Ginseng and *Ganoderma* were sliced, and the fermented *Cordyceps sinensis* powder was put in a cloth bag. The above four drugs were soaked in water for 1 h, and decocted 2 times by heating. The first decoction lasted for 2 h with a 12-fold amount of water added, and the second decoction lasted for 1.5 h with an 8-fold amount of water added. The two liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 14

150 g Radix Panacis Quinquefolii, 90 g fermented *Cordyceps sinensis* powder (*Hirsutella hepialid* Chen et Shen), 120 g *Cordyceps*, 200 g *Ganoderma*, and 90 g Flos Rosae Rugosae were weighed out. The Radix Panacis Quinquefolii and *Ganoderma* were sliced, and the *Cordyceps* was pulverized and put in a cloth bag together with the fermented *Cordyceps sinensis* powder. The above drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 15

100 g Radix Panacis Quinquefolii, 30 g *Cordyceps,* 200 g *Ganoderma*, and 100 g Flos Rosae Rugosae were weighed out. The Radix Panacis Quinquefolii and *Ganoderma* were sliced, and the *Cordyceps* was pulverized and then put in a cloth bag. The above four drugs were soaked in water for 30 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 16

150 g Radix Panacis Quinquefolii, 30 g fermented *Cordyceps sinensis* powder (*Hirsutella sinensis* Liu, Guo, Yu-et Zeng, sp.nov), 200 g *Ganoderma*, and 100 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 17

90 g Radix Panacis Quinquefolii, 90 g *Cordyceps,* 120 g *Ganoderma*, and 60 g Flos Rosae Rugosae were weighed out. The Radix Panacis Quinquefolii and *Ganoderma* were sliced, and the *Cordyceps* was pulverized and then put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 18

90 g Radix Et Rhizoma Ginseng, 90 g *Cordyceps,* 120 g *Ganoderma*, and 60 g Flos Rosae Rugosae were weighed out. The Radix Et Rhizoma Ginseng and *Ganoderma* were sliced, and the *Cordyceps* was pulverized and then put in a cloth bag. The above four drugs were soaked in water for 30 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 19

90 g Radix Panacis Quinquefolii, 60 g fermented *Cordyceps sinensis* powder (*Cephalosporium sinensis* Chen sp.nov), 120 g *Ganoderma*, and 60 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 20

300 g Radix Panacis Quinquefolii, 400 g *Ganoderma,* 67 g *Cordyceps*, and 300 g Flos Rosae Rugosae were weighed out. The Radix Panacis Quinquefolii and *Ganoderma* were sliced, and the *Cordyceps* was pulverized and then put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 21

300 g Radix Panacis Quinquefolii, 400 g *Ganoderma*, 200 g fermented *Cordyceps sinensis* powder (*Paecilomyces hepialli* Chen et Dai, sp.nov), and 300 g Flos Rosae Rugosae were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 22

500 g Radix Panacis Quinquefolii, 100 g *Cordyceps*, 500 g *Ganoderma*, 500 g Flos Rosae Rugosae and 500 g sporoderm-broken *Ganoderma* spore powder were weighed out. The Radix Panacis Quinquefolii and *Ganoderma* were sliced, and the *Cordyceps* was pulverized and then put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles made by spray drying; auxiliary agents frequently used for tablets and the sporoderm-broken *Ganoderma* spore powder were added thereto and uniformly mixed; and various types of tablets were prepared by conventional processes for tablets.

Example 23

500 g Radix Et Rhizoma Ginseng, 100 g fermented *Cordyceps sinensis* powder (*Paecilomyces sinensis* Chen, Xiao et Shi, sp.nov), 500 g *Ganoderma*, 500 g Flos Rosae Rugosae and 500 g sporoderm-broken *Ganoderma* spore powder were weighed out. The Radix Et Rhizoma Ginseng and *Ganoderma* were sliced, and the fermented *Cordyceps sinensis* powder and the sporoderm-broken *Ganoderma* spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 24

150 g Radix Panacis Quinquefolii, 90 g fermented *Cordyceps sinensis* powder (*Tolypocladium sinensis* C. lan Li), 200 g *Ganoderma*, 90 g Flos Rosae Rugosae and 150 g sporoderm-broken *Ganoderma* spore powder were weighed out. The Radix Panacis Quinquefolii and *Ganoderma* were sliced, and the fermented *Cordyceps sinensis* powder was put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles made by spray drying; auxiliary agents frequently used for tablets and the *Ganoderma* spore powder were added thereto and uniformly mixed; and various types of tablets were prepared by conventional processes for tablets.

Example 25

150 g Radix Panacis Quinquefolii, 90 g fermented *Cordyceps sinensis* powder (*Hirsutella hepialid* Chen et Shen), 200 g *Ganoderma*, 90 g Flos Rosae Rugosae and 400 g Radix *Codonopsis* were weighed out. The Radix Panacis Quinquefolii, *Ganoderma* and Radix *Codonopsis* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 26

150 g Radix Panacis Quinquefolii, 120 g *Cordyceps*, 200 g *Ganoderma*, 90 g Flos Rosae Rugosae and 400 g Radix Astragali were weighed out. The Radix Panacis Quinquefolii, *Ganoderma* and Radix Astragali were sliced, and the *Cordyceps* was pulverized and then put in a cloth bag. The above five drugs were soaked in water for 20 min, and decocted 3 times by heating. The first decoction lasted for 2 h, and the following decoctions each lasted for 1 h, with a 14-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for lozenges were added thereto and uniformly mixed, and lozenges were prepared by conventional processes for lozenges.

Example 27

500 g Radix Panacis Quinquefolii, 50 g fermented *Cordyceps sinensis* powder (*Paecilomyces hepialli* Chen et Dai, sp.nov), 50 g fermented *Cordyceps sinensis* powder (*Hirsutella sinensis* Liu, Guo, Yu-et Zeng, sp.nov), 500 g *Ganoderma*, 500 g Flos Rosae Rugosae and 300 g Radix *Codonopsis* were weighed out. The Radix Panacis Quinquefolii, *Ganoderma* and Radix *Codonopsis* were sliced, and the fermented *Cordyceps sinensis* powders were put in a cloth bag. The above five drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for powder were added thereto and uniformly mixed; and powder was prepared by conventional processes for powder.

Example 28

500 g Radix Panacis Quinquefolii, 100 g *Cordyceps*, 500 g *Ganoderma*, 500 g Flos Rosae Rugosae and 300 g Radix Astragali were weighed out. The Radix Panacis Quinquefolii, *Ganoderma* and Radix Astragali were sliced, and the *Cordyceps* was pulverized and then put in a cloth bag. The above five drugs were soaked in water for 20 min, and decocted 3 times by heating. The first decoction lasted for 2 h, and the following decoctions each lasted for 1 h, with a 14-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 29

100 g Radix Panacis Quinquefolii, 200 g *Ganoderma*, 30 g *Cordyceps*, 3 g fermented *Cordyceps sinensis* powder (Cs-C-Q80 *Hirsutella sinensis* Liu, Guo, Yu-et Zeng, sp.nov), 100 g Flos Rosae Rugosae and 100 g *Ganoderma* spore powder were weighed out. The Radix Panacis Quinquefolii and *Ganoderma* were sliced, and the *Cordyceps* was pulverized and put in a cloth bag together with the *Ganoderma* spore powder. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 30

100 g Radix Panacis Quinquefolii, 200 g *Ganoderma*, 30 g fermented *Cordyceps sinensis* powder (*Mortiscrslla hepialid* C. T.& B. liu), 100 g Flos Rosae Rugosae and 100 g *Ganoderma* spore powder were weighed out. The Radix Panacis Quinquefolii and *Ganoderma* were sliced, and the fermented *Cordyceps sinensis* powder and the *Ganoderma* spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills were added thereto and uniformly mixed; and various types of pills were prepared by conventional processes for pills.

Example 31

100 g Radix Panacis Quinquefolii, 200 g *Ganoderma*, 30 g *Cordyceps*, 100 g Flos Rosae Rugosae and 200 g Radix Pseudostellariae were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, auxiliary agents frequently used for soft extracts were added thereto and uniformly mixed, and a soft extract was prepared by conventional processes for soft extracts.

Example 32

100 g Radix Panacis Quinquefolii, 200 g *Ganoderma*, 30 g *Cordyceps*, 100 g Flos Rosae Rugosae and 200 g Radix Pseudostellariae were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 33

100 g Radix Panacis Quinquefolii, 200 g *Ganoderma*, 30 g fermented *Cordyceps sinensis* powder (*Mortierella* sp.), 100 g Flos Rosae Rugosae and 200 g Radix *Codonopsis* were weighed out. The Radix Panacis Quinquefolii, *Ganoderma* and Radix *Codonopsis* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 34

100 g Radix Panacis Quinquefolii, 200 g *Ganoderma*, 30 g fermented *Cordyceps sinensis* powder (*Verticillium sinens* Wamg sp.nov), 100 g Flos Rosae Rugosae and 200 g Radix Astragali were weighed out. The Radix Panacis Quinquefolii, *Ganoderma* and Radix Astragali were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for capsules were added thereto and uniformly mixed; and capsules were prepared by conventional processes for capsules.

Example 35

90 g Radix Panacis Quinquefolii, 120 g *Ganoderma*, 30 g fermented *Cordyceps sinensis* powder (*Cephalosporium sinensis* Chen sp.nov), 30 g fermented *Cordyceps sinensis* powder (*Synnematium sinensis* Yin & Shen), and 60 g Flos Rosae Rugosae were weighed out. The Radix Panacis Quinquefolii and *Ganoderma* were sliced, and the fermented *Cordyceps sinensis* powders were put in a cloth bag. The above four drugs were soaked in water for 1 h, and decocted 3 times by heating. The first decoction lasted for 2 h, and the following decoctions each lasted for 1 h, with a 13-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills were added thereto and uniformly mixed; and various types of pills were prepared by conventional processes for pills.

Example 36

90 g Radix Panacis Quinquefolii, 120 g *Ganoderma*, 90 g *Cordyceps*, 60 g Flos Rosae Rugosae and 200 g Radix Astragali were weighed out. The Radix Panacis Quinquefolii, *Ganoderma* and Radix Astragali were sliced, and the *Cordyceps* was pulverized and then put in a cloth bag. The above five drugs were soaked in water for 40 min, and decocted 3 times by heating. The first decoction lasted for 2 h with a 12-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 37

300 g Radix Panacis Quinquefolii, 400 g *Ganoderma*, 200 g fermented *Cordyceps sinensis* powder (*Scytalidium hepialii* C. L. Li), 300 g Flos Rosae Rugosae and 400 g *Ganoderma* spore powder were weighed out. The Radix Panacis Quinquefolii and *Ganoderma* were sliced, and the *Cordyceps* was pulverized and then put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the *Ganoderma* spore powder were added thereto and uniformly mixed; and various types of tablets were prepared by conventional processes for tablets.

Example 38

300 g Radix Panacis Quinquefolii, 400 g *Ganoderma*, 200 g fermented *Cordyceps sinensis* powder (*Cephalosporium sinens* Chen sp.nov), 300 g Flos Rosae Rugosae and 400 g Radix Pseudostellariae were weighed out. The Radix Panacis Quinquefolii and *Ganoderma* were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 39

300 g Radix Panacis Quinquefolii, 400 g *Ganoderma*, 67 g *Cordyceps*, 300 g Flos Rosae Rugosae and 400 g Radix Pseudostellariae were weighed out. The Radix Panacis Quinquefolii and *Ganoderma* were sliced, and the *Cordyceps* was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 40

300 g Radix Panacis Quinquefolii, 400 g *Ganoderma*, 100 g fermented *Cordyceps sinensis* powder (*Chrysosporium sinens* Z. Q. liang), 100 g fermented *Cordyceps sinensis* powder (*Hirsutella sinensis* Liu, Guo, Yu-et Zeng, sp.nov), and 300 g Flos Rosae Rugosae were weighed out. The Radix Panacis Quinquefolii and *Ganoderma* were sliced, and the fermented *Cordyceps sinensis* powders were put in a cloth bag. Upon addition of 55% ethanol, the drugs were extracted twice under reflux, with each extraction lasting for 1 h. Then the liquid extracts were combined, and ethanol was recovered to obtain the alcohol extract. The residual drugs were further decocted twice in water by heating. The first decoction lasted for 2 h, and the following decoction lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 41

300 g Radix Panacis Quinquefolii, 400 g *Ganoderma*, 67 g *Cordyceps*, 20 g fermented *Cordyceps sinensis* powder (*Hirsutella sinensis* Liu, Guo, Yu-et Zeng, sp.nov), and 300 g Flos Rosae Rugosae were weighed out. The Radix Panacis Quinquefolii and *Ganoderma* were sliced, and the *Cordyceps* was pulverized and then put in a cloth bag. Upon addition of 75% ethanol, the drugs were extracted for 2 h under reflux, and ethanol was recovered to obtain the alcohol extract. The residual drugs were further decocted three times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 42

300 g Radix Et Rhizoma Ginseng, 400 g *Ganoderma*, 200 g fermented *Cordyceps sinensis* powder (*Cephalosporium acremonium* Corda, Icones Fungorum), 300 g Flos Rosae Rugosae and 400 g Radix *Codonopsis* were weighed out. The Radix Et Rhizoma Ginseng, *Ganoderma* and Radix *Codonopsis* were sliced, and the fermented *Cordyceps sinensis* powder was put in a cloth bag. Upon addition of 15% ethanol, the drugs were extracted twice under reflux, with each extraction lasting for 1 h. Then the liquid extracts were combined, and ethanol was recovered to obtain the alcohol extract. The residual drugs were further decocted 3 times in water by heating. The first decoction lasted for 2 h, and the following decoctions lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 43

300 g Radix Et Rhizoma Ginseng, 400 g *Ganoderma*, 200 g fermented *Cordyceps sinensis* powder (*Sporothrix insectorum* de Hong & H. C. Evans), 300 g Flos Rosae Rugosae and 400 g Radix *Codonopsis* were weighed out. The Radix Et Rhizoma Ginseng and *Ganoderma* were sliced, and the *Cordyceps* was pulverized and put in a cloth bag. Upon addition of 95% ethanol, the drugs were extracted under reflux for 2 h, and ethanol was recovered to obtain the alcohol extract. The residual drugs were further decocted 3 times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 44

300 g Radix Et Rhizoma Ginseng, 400 g *Ganoderma*, 67 g *Cordyceps*, 300 g Flos Rosae Rugosae, 300 *Ganoderma* spore powder and 400 g Radix Astragali were weighed out. The Radix Et Rhizoma Ginseng and *Ganoderma* were sliced, and the *Cordyceps* was pulverized and then put in a cloth bag. Upon addition of 5% ethanol, the drugs were extracted under reflux for 2 h, and ethanol was recovered to obtain the alcohol extract. The residual drugs were further decocted twice in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 45

300 g Radix Panacis Quinquefolii, 400 g *Ganoderma*, 200 g fermented *Cordyceps sinensis* powder (*Isaria farinose* (Holmsk.) Fr.Systema Mycologicum), 300 g Flos Rosae Rugosae and 400 g Radix Astragali were weighed out. The Radix Panacis Quinquefolii and *Ganoderma* were sliced, and the fermented *Cordyceps sinensis* powder was put in a cloth bag. Upon addition of 60% ethanol, the drugs were extracted twice under reflux for 2 h, with each extraction lasting for 1 h. Then the liquid extracts were combined, and ethanol was recovered to obtain the alcohol extract. The residual drugs were further decocted 3 times in water by heating. The first decoction lasted for 2 h, and the following decoctions lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

The invention claimed is:
1. A method for treating AIDS in a human in need thereof consisting essentially of administering to the human in need thereof a composition consisting of:

a) 5 to 200 parts by weight of *Ganoderma*;
b) 5 to 150 parts by weight of Radix Panacis Quinquefolii or 5 to 150 parts by weight of Radix Et Rhizoma Ginseng;
c) 1 to 90 parts by weight of fermented *Cordyceps sinensis* powder and/or 1 to 120 parts by weight of *Cordyceps*; and
d) a component selected from the group consisting of 5 to 90 parts by weight of Flos Rosae Rugosae, 5 to 150 parts by weight of *Ganoderma* spore powder, 10 to 400 parts by weight of Radix Pseudostellariae, 3 to 400 parts by weight of Radix *Codonopsis*, 3 to 400 parts by weight of Radix Astragali and mixtures thereof.

2. The method of claim 1, wherein components (a)-(c) of the composition consist of:
(a) 20 to 120 parts by weight of *Ganoderma*,
(b) 10 to 90 parts by weight of Radix Panacis Quinquefolii or Radix Et Rhizoma Ginseng, and
(c) a *Cordyceps* material selected from the group consisting of:
(i) 3 to 60 parts by weight of fermented *Cordyceps sinensis* powder,
(ii) 3 to 90 parts by weight of *Cordyceps*, and
(iii) mixtures of (i) and (ii).

3. The method of claim 1, wherein components (a)-(c) of the composition consist of:
(a) 40 parts by weight of *Ganoderma*,
(b) 30 parts by weight of Radix Panacis Quinquefolii or Radix Et Rhizoma Ginseng, and
(c) a *Cordyceps* material selected from the group consisting of:
(i) 20 parts by weight of fermented *Cordyceps sinensis* powder, and/or
(ii) 6.7 parts by weight of *Cordyceps*, and
(iii) mixtures of (i) and (ii).

4. The method of claim 1, further consisting essentially of one or more of the following:
(a) 10 to 60 parts by weight of Flos Rosae Rugosae,
(b) 10 to 120 parts by weight of *Ganoderma* spore powder,
(c) 20 to 200 parts by weight of Radix Pseudostellariae,
(d) 20 to 200 parts by weight of Radix *Codonopsis*, and
(e) 20 to 200 parts by weight of Radix Astragali.

5. The method of claim 1, further consisting essentially of one or more of the following:
(a) 30 parts by weight of Flos Rosae Rugosae,
(b) 30 parts by weight of *Ganoderma* spore powder,
(c) 40 parts by weight of Radix Pseudostellariae,
(d) 40 parts by weight of Radix *Codonopsis*, and
(e) 40 parts by weight of Radix Astragali.

6. The method of claim 1, wherein component (d) of the composition consists of 5 to 90 parts by weight of Flos Rosae Rugosae.

7. The method of claim 2, wherein component (d) of the composition consists of 10 to 60 parts by weight of Flos Rosae Rugosae.

8. The method of claim 3, wherein component (d) of the composition consists of 30 parts by weight of Flos Rosae Rugosae.

9. The method of claim 1, wherein the composition is in a form selected from the group consisting of a tablet, an oral liquid, a granule, a capsule, an electuary, a dripping pill, a pill, powder, a lozenge, an injection, and a syrup.

10. The method of claim 1, wherein the fermented *Cordyceps sinensis* powder is selected from the group consisting of *Paecilomyces hepialli* Chen et Dai, sp.nov, *Mortiscrslla hepialid* C.T.&B.liu, *Synnematium sinensis* Yin & Shen, *Gliocladium roseum* (link) Thom, *Mortierella* sp., *Cephalosporium sinensis* Chen sp.nov or *Hirsutella sinensis* Liu, Guo, and Yu-et Zeng, sp.nov.

11. The method of claim 1, wherein the *Ganoderma* spore powder is sporoderm-broken *Ganoderma* spore powder.

12. A method for treating AIDS in a human in need thereof consisting essentially of administering to the human in need thereof a composition consisting of a water extract, an alcohol extract, or a combination of a water extract and an alcohol extract of the following materials:
a) 5 to 200 parts by weight of *Ganoderma*;
b) 5 to 150 parts by weight of Radix Panacis Quinquefolii or 5 to 150 parts by weight of Radix Et Rhizoma Ginseng;
c) 1 to 90 parts by weight of fermented *Cordyceps sinensis* powder and/or 1 to 120 parts by weight of *Cordyceps*; and
d) a component selected from the group consisting of 5 to 90 parts by weight of Flos Rosae Rugosae, 5 to 150 parts by weight of *Ganoderma* spore powder, 10 to 400 parts by weight of Radix Pseudostellariae, 3 to 400 parts by weight of Radix *Codonopsis*, 3 to 400 parts by weight of Radix Astragali and mixtures thereof.

13. The method of claim 12, wherein component (d) of the composition consists of 5 to 90 parts by weight of Flos Rosae Rugosae.

14. The method of claim 12, wherein components (a)-(c) of the composition consist of:
(a) 20 to 120 parts by weight of *Ganoderma*;
(b) 10 to 90 parts by weight of Radix Panacis Quinquefolii or Radix Et Rhizoma Ginseng; and
(c) a *Cordyceps* material selected from the group consisting of:
(i) 3 to 60 parts by weight of fermented *Cordyceps sinensis* powder;
(ii) 3 to 90 parts by weight of *Cordyceps*; and
(iii) mixtures of (i) and (ii).

15. The method of claim 14, wherein component (d) of the composition consists of 10 to 60 parts by weight of Flos Rosae Rugosae.

16. The method of claim 12, wherein components (a)-(c) of the composition consist of:
(a) 40 parts by weight of *Ganoderma*,
(b) 30 parts by weight of Radix Panacis Quinquefolii or Radix Et Rhizoma Ginseng, and
(c) a *Cordyceps* material selected from the group consisting of:
(i) 20 parts by weight of fermented *Cordyceps sinensis* powder;
(ii) 6.7 parts by weight of *Cordyceps*; and
(iii) mixtures of (i) and (ii).

17. The method of claim 16, wherein component (d) of the composition consists of 30 parts by weight of Flos Rosae Rugosae.

18. The method of claim 12, further consisting essentially of one or more of the following:
(a) 10 to 60 parts by weight of Flos Rosae Rugosae,
(b) 10 to 120 parts by weight of *Ganoderma* spore powder,
(c) 20 to 200 parts by weight of Radix Pseudostellariae,
(d) 20 to 200 parts by weight of Radix *Codonopsis*, and
(e) 20 to 200 parts by weight of Radix Astragali.

19. The method of claim 18, further consisting essentially of one or more of the following:
(a) 30 parts by weight of Flos Rosae Rugosae,
(b) 30 parts by weight of *Ganoderma* spore powder,
(c) 40 parts by weight of Radix Pseudostellariae, (d) 40 parts by weight of Radix *Codonopsis*, and (e) 40 parts by weight of Radix Astragali.

20. The method of claim 12, wherein the composition is formulated in a form selected from the group consisting of a tablet, an oral liquid, a granule, a capsule, an electuary, a dripping pill, a pill, powder, a lozenge, a fluid extract, an injection, and a syrup.

21. The method of claim 12, wherein the fermented *Cordyceps sinensis* powder is selected from the group consisting of *Paecilomyces hepialli* Chen et Dai, sp.nov, *Mortiscrslla hepialid* C.T.&B.liu, *Synnematium sinensis* Yin & Shen, *Gliocladium roseum* (link) Thom, *Mortierella* sp., *Cephalosporium sinensis* Chen sp.nov or *Hirsutella sinensis* Liu, Guo, and Yu-et Zeng, sp.nov.

22. The method of claim 12, wherein the *Ganoderma* spore powder is sporoderm-broken *Ganoderma* spore powder.

23. The method of claim 12, wherein the components of the composition are extracted with ethanol at a concentration of 5% to 95%.

24. The method of claim 12, wherein the composition consists of both a water extract and an alcohol extract.

\* \* \* \* \*